US010309883B2

(12) United States Patent
Rassaian et al.

(10) Patent No.: US 10,309,883 B2
(45) Date of Patent: Jun. 4, 2019

(54) ANALYZING STRUCTURAL DURABILITY IN THE FREQUENCY DOMAIN

(71) Applicant: THE BOEING COMPANY, Chicago, IL (US)

(72) Inventors: Mostafa Rassaian, Bellevue, WA (US); Jonathan H. Gosse, Issaquah, WA (US); Stephen Christensen, Sammamish, WA (US)

(73) Assignee: THE BOEING COMPANY, Chicago, IL (US)

( * ) Notice: Subject to any disclaimer, the term of this patent is extended or adjusted under 35 U.S.C. 154(b) by 1012 days.

(21) Appl. No.: 14/554,486

(22) Filed: Nov. 26, 2014

(65) Prior Publication Data

US 2015/0112657 A1    Apr. 23, 2015

Related U.S. Application Data

(63) Continuation of application No. 11/948,880, filed on Nov. 30, 2007, now Pat. No. 9,020,786.

(51) Int. Cl.
  *G06F 17/50* (2006.01)
  *G01N 3/32* (2006.01)
  (Continued)

(52) U.S. Cl.
  CPC ............. *G01N 3/32* (2013.01); *G01N 29/045* (2013.01); *G01N 29/12* (2013.01);
  (Continued)

(58) Field of Classification Search
  None
  See application file for complete search history.

(56) References Cited

U.S. PATENT DOCUMENTS 5,305,645 A     4/1994  Reifsnider et al.
5,447,765 A *   9/1995  Crane ................... B29C 53/585
                                              242/430
(Continued)

FOREIGN PATENT DOCUMENTS

EP      2065694 A2      6/2009

OTHER PUBLICATIONS

S. W. Tsai, J. L. Townsley, "Methodology for Composite Durability Assessment" Sep. 2003, pp. 1-34.*
(Continued)

*Primary Examiner* — Kibrom K Gebresilassie
(74) *Attorney, Agent, or Firm* — Patterson + Sheridan, LLP

(57) ABSTRACT

A method of analyzing the durability of a structure. Load-controlled testing is performed on samples of a composite material of the structure to relate critical strain invariants of the material to cyclic rates of strain invariant accumulation and frequencies associated with the cyclic rates. The material is characterized based on effective properties of the material, including the cyclic rates of strain invariant accumulation. Laminate properties and a geometrical definition of the structure are used to obtain a parametric model. Material characterizations are used to determine model element frequency responses to applied load conditions. Each element's frequency responses and critical strain invariants are used to determine whether damage is indicated at the element. Progression of damage is tracked and accounted for in the model.

21 Claims, 3 Drawing Sheets

(51) Int. Cl.
 G01N 29/04 (2006.01)
 G01N 29/12 (2006.01)
 B29C 65/00 (2006.01)
 B64C 1/00 (2006.01)
(52) U.S. Cl.
 CPC ...... *G06F 17/5009* (2013.01); *G06F 17/5018* (2013.01); *G06F 17/5086* (2013.01); *G06F 17/5095* (2013.01); *B29C 66/721* (2013.01); *B29C 66/7212* (2013.01); *B64C 2001/0072* (2013.01); *G01N 2291/02827* (2013.01); *G06F 2217/44* (2013.01); *Y02T 50/43* (2013.01)

(56) References Cited

U.S. PATENT DOCUMENTS

| | | | | |
|---|---|---|---|---|
| 5,744,221 | A * | 4/1998 | Crane | E04C 3/29 242/430 |
| 6,363,789 | B1 | 4/2002 | Rassaian et al. | |
| 6,678,627 | B1 | 1/2004 | Starr | |
| 7,010,472 | B1 * | 3/2006 | Vasey-Glandon | G06F 17/50 700/97 |
| 7,120,544 | B2 | 10/2006 | Duncan | |
| 7,203,628 | B1 | 4/2007 | St. Ville | |
| 2007/0062291 | A1 * | 3/2007 | Mitchell | G01M 7/08 73/649 |
| 2007/0100565 | A1 * | 5/2007 | Gosse | G06F 17/5018 702/34 |
| 2007/0220454 | A1 * | 9/2007 | Rassaian | G06F 17/5009 703/1 |
| 2008/0141072 | A1 | 6/2008 | Kalgren et al. | |
| 2011/0218743 | A1 * | 9/2011 | Smith | G01N 29/11 702/56 |
| 2014/0019091 | A1 * | 1/2014 | Higgins | G06F 15/00 702/184 |

OTHER PUBLICATIONS

A. Kuraishi, J. H. Gosse, "Methodology for Composite Durability Assessment" 2002, pp. 1-32.*
S. W. Tsai, J. L. Townsley, "Methodology for Composite Durability Assessment", Sep. 2003, pp. 1-34 (Year: 2003).*
A. Kuraishi, J. H. Gosse, "Methodology for Composite Durability Assessment" 2002, pp. 1-32 (Year: 2002).*
Search Report for European Patent Application EP 2065694 A3, Application No. 08170018.9, dated Feb. 14, 2014.
Arief Yudhanto, NPL, "Effects of Micromechanical Factors in the Strain Invariant Failure Theory for Composites", 2005.
Akira Kuraishi, Jonathan H. Gosse, Jeffrey A. Wollschlager, John L. Townsley, "Methodology for Composite Durability Assessment", 2002.
Stephen A. Rizzi, Adam Przekop, "Estimation of Sonic fatigue by reduced-Order Finite Element Based Analyses", Jul. 2006.
T.E. Tay, V.B.C. Tan and S.H.N. Tan, "Element-Failure: An Alternative to Material Property Degradation Method for Progressive Damage in Composite Structures", Journal of Composite Materials 2005.
Adam Przekop, Stephen A. Rizzi, "An Investigation of High Cycle Fatigue Models for Metallic Structures Exhibiting Snap-Through Response", AIAA, Apr. 2007.
Izhak Bucher, "Parametric Optimization of Structures Under Combined Base Motion Direct Forces and Static Loading", Transactions of the ASME, vol. 124, Jan. 2002, pp. 132-140.
Michael Allen, Nickolas Vlahopoulos, "Noise generated from a flexible and elastically supported structure subject to turbulent boundary layer flow excitation", Elsevier, Finite Elements in Analysis and Design 37 (2001); pp. 687-712.
PCT International Search Report and Written Opinion of the International Searching Authority, International application No. PCT/US2007/006523; dated May 23, 2008.
Gosse, "Strain Invariant Failure Theory: Failure Theory and Methodologies for Implementation," http://www.composition.neVDownloads/Presentation%20-%20Modelling%20-%20Boeing.pdf; 16 pages.
Gosse, "A Damage Functional Methodology for Assessing Post-Damage Initiation Environments in Composite Structure," American Institute of Aeronautics and Astronautics; pp. 1-5; Apr. 2004.
Tay, et al., Damage progression by the element-failure method (EFM) and strain invariant failure theory (SIFT); Composites Science and Technology, vol. 65, pp. 935-944; 2004.
Li, et al., "Application of a First Invariant Strain Criterion for Matrix Failure in Composite Materials," Journal of Composite Materials, vol. 37, No. 22, pp. 1977-2000; Apr. 2003.
Tsai, et al., "Methodology for Composite Durability Assessment," SAMPE Technical Conference, Dayton, Ohio; Sep. 2003.
Barlow, "Optimal Stress Locations in Finite Element Models," International Journal for Numerical Methods in Engineering, vol. 10, pp. 243-251 ; 1976.
Barlow, "More on Optimal Stress Points—Reduced Integration, Element Distortions and Error Estimation," International Journal for Numerical Methods in Engineering, vol. 28, No. 7, pp. 1487-1504; Jul. 1989.
Li, et al., "Low-velocity impact-induced damage of continuous fibeNeinforced composite laminates. Part I. An FEM numerical model," Composites Part A: Applied Science and Manufacturing, vol. 33, No. 8, pp. 1055-1062; Aug. 1, 2002.
Causkan, "Axial & Lateral Impact Prediction of Composite Structures Using Explicit Finite Element Analysis," Proceedings of the International Mechanical Engineering Congress and Exposition, pp. 41-49; 2002.
Search Report and Written Opinion for PCT/US2006/043074 dated Mar. 21,2007.
Tay et al., "Element-Failure: An Alternative to Material Property Degradation Method for Progressive Damage in Composite Structures," Journal of Composite Materials, vol. 39, No. 18, pp. 1659-1675; Jun. 14, 2005.
Caruthers et al., "A Thermodynamically Consistent, Nonlinear Viscoelastic Approach for Modeling Glassy Polymers," Polymer, vol. 45, pp. 4577-4597; 2004.
Adolf et al., "Extensive Validation of a Thermodynamically Consistent, Nonlinear Viscoelastic Model for Glassy Polymers," Polymer, vol. 45, pp. 4599-4621; 2004.

* cited by examiner

ANALYZING STRUCTURAL DURABILITY IN THE FREQUENCY DOMAIN

CROSS-REFERENCE TO RELATED APPLICATIONS

This application is a continuation of U.S. patent application Ser. No. 11/948,880 filed Nov. 30, 2007, Now U.S. Pat. No. 9,020,786, and is related to U.S. patent application Ser. No. 11/375,225 filed on Mar. 14, 2006, Now U.S. Pat. No. 7,925,475, and U.S. patent application Ser. No. 11/555,873 filed on Nov. 2, 2006. Each of the disclosures of the above applications is incorporated herein by reference in its entirety.

FIELD

The present disclosure relates generally to designing structures and more particularly (but not exclusively) to frequency-domain analysis of the durability of structures, including but not limited to structures that include composite materials.

BACKGROUND

The statements in this section merely provide background information related to the present disclosure and may not constitute prior art.

Composite materials are incorporated into many structures, including but not limited to commercial aircraft. Composite materials typically are formed by disposing fiber and/or other material in a polymer matrix. The composite may be laid as tape or strips in varying directions and layers and cured to form a structure. The behavioral characteristics of composite materials over time in response to loads can be difficult to predict relative to structures in which they are incorporated.

SUMMARY

In one implementation, the present disclosure is directed to a method of analyzing the durability of a structure. For each of one or more materials of the structure, load-controlled testing is performed on one or more samples of the material to relate each of a plurality of critical strain invariants of the material to cyclic rates of strain invariant accumulation and frequencies associated with the cyclic rates. Each material is characterized based on effective properties of the material. The properties include but are not necessarily limited to the cyclic rates of strain invariant accumulation. The method includes using laminate properties of the material(s) and a geometrical definition of the structure to obtain a parametric model including a plurality of elements. Load conditions are applied to the model and the material characterizations are used to determine frequency responses of the elements to the load conditions. For each element, the determined frequency responses and the critical strain invariants are used to determine whether damage is indicated at the element.

In another implementation, the disclosure is directed to a system for analyzing the durability of a structure. The system includes at least one processor and memory configured to characterize each of one or more materials of the structure based on effective properties of the material. The properties include, for each of a plurality of critical strain invariants of the material, a plurality of cyclic rates of strain invariant accumulation and frequencies associated with the cyclic rates. The processor and memory are configured to use laminate properties of the material(s) and a geometrical definition of the structure to obtain a parametric model including a plurality of elements. The processor and memory are further configured to apply load conditions to the model, use the material characterizations to determine frequency responses of the elements to the load conditions, and for each element, use the determined frequency responses and the critical strain invariants to determine whether damage is indicated at the element.

In yet another implementation, the disclosure is directed to a computer-readable medium for use in analyzing the durability of a structure. The medium includes computer-executable instructions for characterizing each of one or more materials of the structure based on effective properties of the material. The properties include, for each of a plurality of critical strain invariants of the material, a plurality of cyclic rates of strain invariant accumulation and frequencies associated with the cyclic rates. The medium includes computer-executable instructions for using laminate properties of the material(s) and a geometrical definition of the structure to obtain a parametric model including a plurality of elements, applying load conditions to the model, and using the material characterizations to determine frequency responses of the elements to the load conditions. Instructions are provided which are computer-executable to use, for each element, the determined frequency responses and the critical strain invariants to determine whether damage is indicated at the element, to use strain tensors of the elements to analyze progression of indicated damage relative to the elements, and to account for the progression in the model.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

In various implementations of the disclosure, a finite element-based analysis system is provided that can be used to analyze progressive fatigue in composite materials. Such fatigue may result under quasi-static and/or cyclic loading. Loads may include quasi-static and/or vibrational loading due to base excitation and/or acoustic loading, including preload due to thermal and/or static pressure. Although various implementations are described with reference to composite materials, it should be noted that the disclosure may be implemented relative to various types of materials and structures that may or may not include composite materials.

Figure 1:
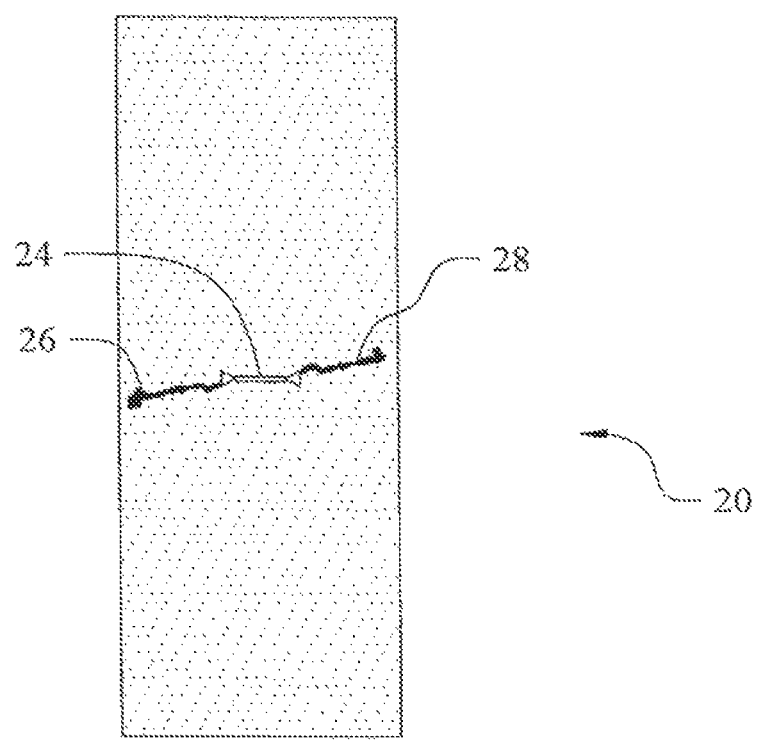
FIG. 1 illustrates a laminate sample exhibiting damage.

A laminate sample is indicated generally in FIG. 1 by reference number 20. The sample 20 has a central slot 24 and exhibits tension-caused damage areas 26 and 28. It can be seen that the damage is diffused. Generally, fatigue in composite laminates tends to be complex. Damage in composite materials is typically diffused and characterized by multiple matrix cracks and delamination. Simulating composite fatigue as a single crack and using traditional fracture mechanics are generally not effective where a single crack tip cannot be identified. Moreover, parts of damaged composite structures often remain capable of partially transmitting loads.

In some implementations of the present disclosure, composite materials may be simulated under dynamic load in order to analyze onset and propagation of damage. In various implementations, analysis is performed in the frequency domain. As further described below, effects of loading on a structure past reversible behavior and to the point of damage may be analyzed in accordance with a physics-based, strain invariant failure theory. Furthermore, initiation and propagation of damage may be iteratively analyzed in accordance with strain invariant failure theory and the damage automatically accounted for in the simulation. "Damage", or failure, is defined in this disclosure as the onset of irreversible behavior.

Figure 2:
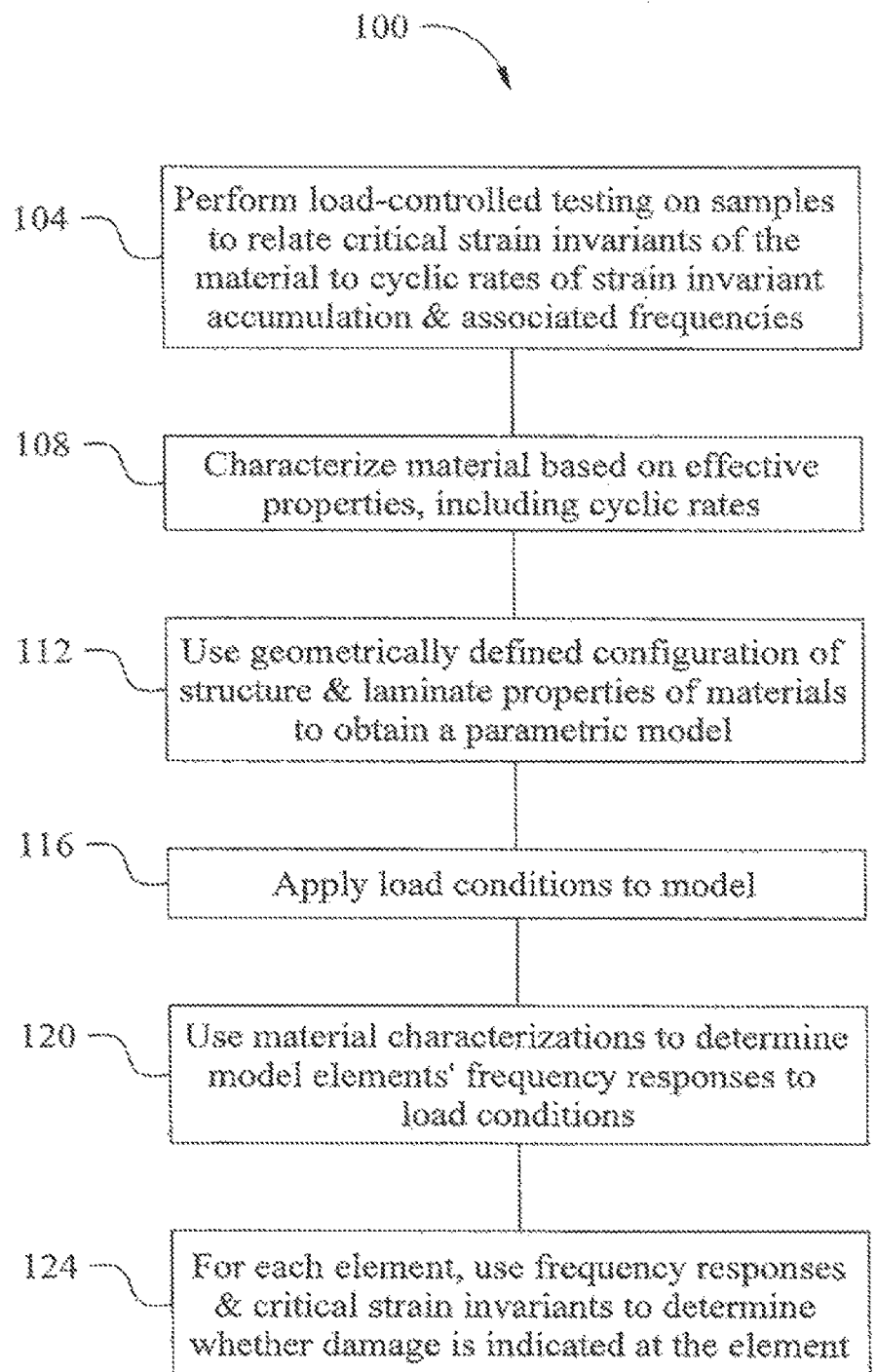
FIG. 2 is a flow diagram of a method of analyzing the durability of a structure in accordance with one implementation of the disclosure.

In one implementation, the disclosure is directed to a method of analyzing the durability of a structure, indicated generally in FIG. 2 by reference number 100. In process 104, for each of one or more materials of the structure, load-controlled testing is performed on samples of the material to relate each of a plurality of critical strain invariants of the material to cyclic rates of strain invariant accumulation and frequencies associated with the cyclic rates. Coupon testing is performed to obtain a set of fatigue/damage curves relating cycles to failure and critical values of strain invariants of the material.

In process 108, each material is characterized based on effective properties of the material. The properties include but are not necessarily limited to the cyclic rates of strain invariant accumulation. In process 112, laminate properties of the material(s) and a geometrical definition of the structure are used to obtain a parametric model including a plurality of elements. In process 116, load conditions are applied to the model. In process 120, the material characterizations are used to determine frequency responses of the elements to the load conditions. In process 124, for each element, the determined frequency responses and the critical strain invariants are used to determine whether damage is indicated at the element. It should be noted that performance of at least some of the processes of the method 100 can be iterative, and that various processes of the method 100 may be performed simultaneously and/or in an order different from that shown in FIG. 2. It also should be noted generally that processes described in this disclosure and claims are exemplary only. A "process" could include a single operation, a plurality of operations, and/or operations different than as described with reference to exemplary implementations.

In some implementations, analysis in accordance with the method 100 can be continued after onset of damage is indicated. Analysis can be performed iteratively to determine whether and, if so, how, the indicated damage would progress in the material and the structure. More specifically, strain tensors of the model elements are used to determine where and to what extent a progression of damage relative to the elements is indicated. Where progression of damage is indicated, force of the damage progression as it affects the elements of the model can be iteratively accounted for in the model.

The critical invariants of the composite constituent materials, especially those of the polymeric matrix, are known to be functionals of temperature, loading rate, and the environment (moisture content, fluid content, etc.). These relationships can be quantified through testing of lamina coupons. In various implementations of the disclosure, both quasi-static and cyclic loading may be applied in load control until a defined end point, as determined by the appropriate critical invariant, has been realized.

In various implementations of the disclosure, fatigue failure in composite materials and bond lines is analyzed using an accumulative invariant approach. This approach makes use of cyclic rates for invariant accumulation in a material up to a critical value. In one implementation, cyclic rates are assumed to be a function of both the stress ratio R (defined below) and the applied frequency. It also may be assumed that testing involves the functional nature of the strain invariants (that is, a critical strain invariant value exists for a given temperature, loading rate and environment).

By varying the level of input spectrum and testing to determine corresponding cyclic rates, it is possible to apply these rates to a structural model and assess the results. Various implementations of the disclosure provide a superposition of linear conditions to failure (with a given critical invariant established as the limit to accumulate to). Testing may be used to generate a correlation of the critical invariants of a material to the cyclic rates and their associated frequencies. Linearity and scaling may be performed using the stress ratio R, which is defined as follows:

$$R = Smin/Smax \quad (1)$$

where Smin and Smax represent minimum and maximum stresses respectively under fatigue loading.

Figure 3:
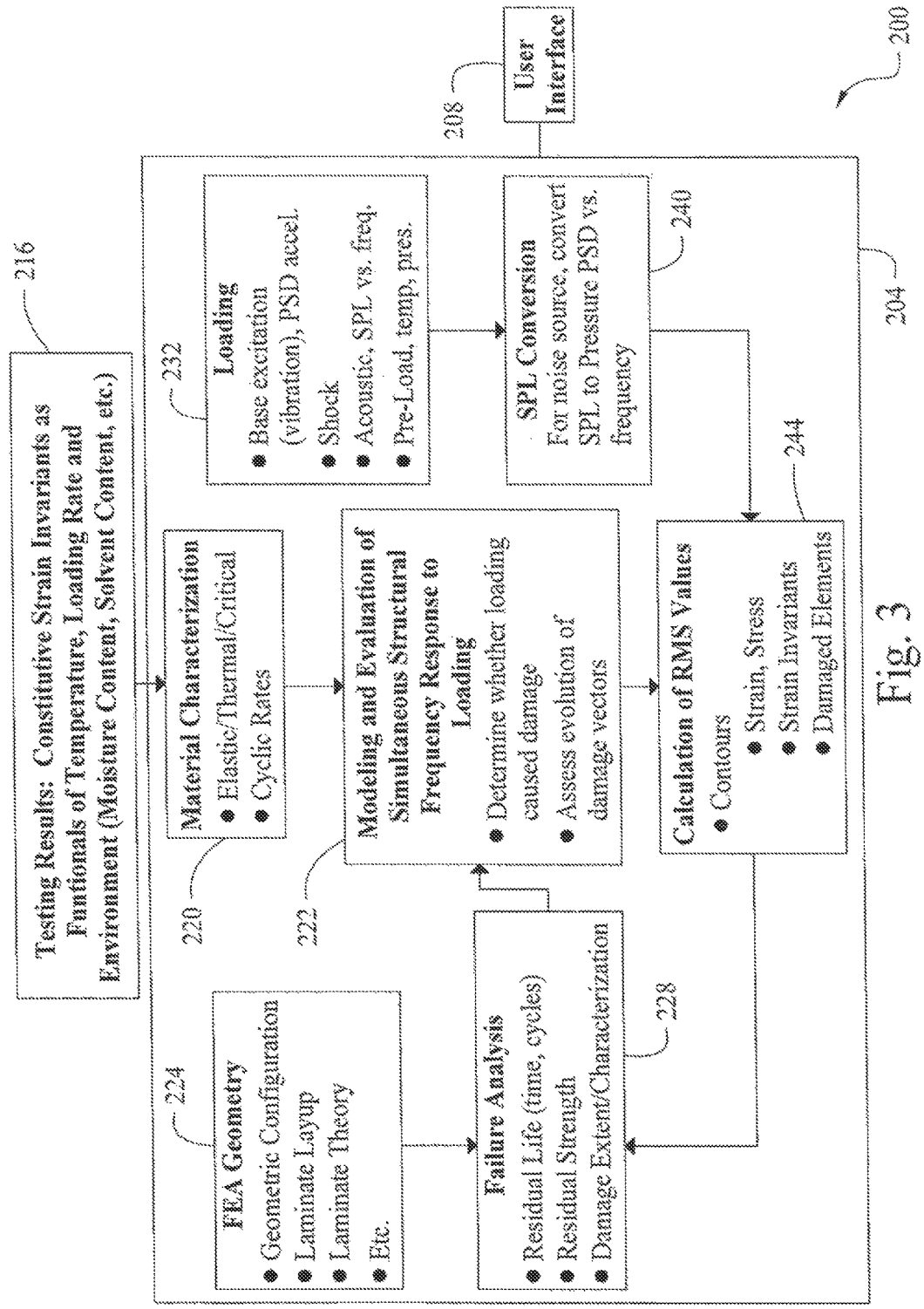
FIG. 3 is a block diagram of a system for analyzing the durability of a structure in accordance with one implementation of the disclosure.

A diagram of a system for analyzing the durability of a structure in accordance with one implementation of the disclosure is indicated generally in FIG. 3 by reference number 200. The system 200 may reside at least in part in one or more computers 204 having one or more processors and memory. It may be desirable in some cases for the system to be implemented using more than one computer, for example, in a distributed environment. For the sake of simplicity, however, the present disclosure shall refer to a single computer. A user interface 208, e.g., a monitor, laptop and/or other display capability may be used to receive user input and/or display output of the system 200. Functionality of the system 200 is represented conceptually in FIG. 3 as a plurality of blocks further described below. In the present exemplary configuration, software resident in memory of the computer(s) 204 may provide much, if not all, of the functionality of the system 200. It should be noted that there are many ways of providing the functionality of the system 200, and that the division of functionality into the following blocks is exemplary only.

Functionality of the system 200 shall be described with reference to a simulation of loading of a structure, e.g., a panel that includes a laminate composite material, e.g., tape. It shall be assumed for simplicity in the present example that tape is the only composite material included in the panel. It should be noted, however, that analysis could include more than one composite material for a structure that includes more than one composite.

As previously discussed, an appropriate number of coupon tests are performed on the tape. Test data includes, and in some cases may be limited to, a simple uni-axial tension test for each of three laminate configurations: [0]n, [10]n and [90]n. Results 216 of the testing include constitutive strain invariants as functionals of temperature, loading rate, and environment (including but not necessarily limited to moisture content and/or fluid content).

The results of coupon testing are input to a block 220, in which properties and cyclic rates of the tape material are extracted from the test results. Material properties defined and used in the system 200 may vary dependent on the material. Where, for example, the material is a unidirectional tape product, properties such as effective lamina (or ply) elastic, thermal and critical properties are extracted from coupon test specimens. By "effective" is meant the mean behavior of the lamina, taking into account all of the phases of the composite and their interactions. In the present example, constitutive phases taken into account are the isotropic homogenous polymeric matrix phase and the homogenous fiber reinforcement phase. The homogenous fiber reinforcement phase refers to either isotropic (glass) or orthotropic (carbon). Effective elastic lamina properties include the three Young's moduli, the three shear moduli and the three Poisson's ratios. Effective thermal properties include the three coefficients of thermal expansion. With respect to these twelve effective properties, seven are independent. The shear modulus of the 2-3 plane is a function of two of these seven independent properties. Effective lamina properties also include critical properties (e.g., critical strain invariants).

"Cyclic rate" refers to the rate of strain invariant accumulation. It is assumed that the same mechanisms that address the emergence of non-conservative forces in quasi-static environments are also involved in cyclic loading environments. For load-controlled environments, it is assumed in the system 200 that composite materials with dissipative constituents would undergo an increase of deformation from every cycle. Accordingly, in some implementations of the disclosure, the cyclic rate is characterized as a unit accumulation as determined by test. In various implementations, the cyclic rate is assumed to be a function of applied frequency and input spectrum (PSD acceleration). Tests conducted in displacement-controlled and load-controlled environments as well as the relative success of Miner's rule suggest that the foregoing approach to assessing fatigue would be appropriate. The limit of accumulation would be the associated critical strain invariant for a given temperature, loading rate and environment (moisture content, solvent content, etc.). It should be noted that in various implementations of simulation in accordance with the disclosure, strain invariant accumulation is allowed to proceed until the critical value of the strain invariant for the material is realized.

In block 222 a numerical method of analysis, e.g., finite element analysis, is performed on a parametric model of the panel as further described below. In a block 224, a geometrical definition of the structure is obtained for use in configuring the model. For example, a user may input structural data via a computer-assisted design (CAD) tool, e.g., Catia, to a FE preprocessor, e.g., PATRAN or Hypermesh, to define the structural geometry of the panel. Loading and displacement boundary conditions associated with the panel are input to the system 200 in the block 224. Effective lamina properties for the tape included in the panel also are input. Generally, if laminate shell elements are to be included in a given structural analysis, [A], [B] and [D] matrices from lamination theory also are input in the block 224. Additionally, an element fiber angle (for solid elements) or an element laminate layup (for laminated shell elements) may be input in the block 224.

At the beginning of an analysis many questions will have been asked, for example: What is the remaining life of the structure? What is the ultimate load carrying capability of the structure? What kind of damage (if any) exists for the questions posed above? Failure analysis, performed in block 228, can consolidate most, if not all, information from the other blocks and produce answers to these questions, e.g., in a pre-determined report form. Failure analysis information can be input to the simulation process further described below and can be iteratively updated during simulation.

In block 232, loading conditions to be input for simulation may be user-specified and/or computer-generated. Loading conditions may include static (including pressure and/or thermal) pre-loads, base excitation (i.e., vibration, which may be random), shock loads, and/or acoustic loads. In block 222, frequency-based fatigue calculations are performed using power spectral density (PSD) function as a basis to represent the input environment as well as the response. Base excitation loads, for example, are analyzed in terms of acceleration PSD. Reference is made to U.S. patent application Ser. No. 11/375,225, filed Mar. 14, 2006, the disclosure of which is incorporated herein by reference in its entirety, in which systems and methods are described for analyzing structural design relative to vibrational and/or acoustic loading in the frequency domain. Various aspects of processing in block 222 may be performed in accordance with various aspects of the disclosure of U.S. patent application Ser. No. 11/375,225.

Typically the most severe acoustic or vibration environment occurs when a structure is under static preload. High static pressure or temperature can induce large mean stresses when compared to dynamic stress levels. In block 222, the simultaneous structural response of a structure to acoustic or vibration with static preload conditions may be evaluated.

In block 222, inputs from blocks 224 and 228 are processed to obtain a finite element (FE) model of the structure. The model includes nodes and elements, e.g., brick and/or shell elements, describing geometry of the structure, e.g., in a format compatible with a three-dimensional finite element tool, e.g., NIKE3D. It should be noted, however, that the disclosure could be implemented in connection with finite element tools other than NIKE3D, for example, NASTRAN, ANSYS, or ABAQUS. The model also includes boundary conditions for loading and displacement associated with the panel.

Loading conditions from block 232 are also input to block 222 for simulation of the FE model. Acoustic load conditions may be input in terms of sound pressure level. In block 240, sound pressure level is converted to an equivalent fluctuating pressure PSD as a function of frequency. The pressure PSD ($psi^2$/Hz) conversion from SPL, G(f) is governed by the equation:

$$G(f) = 8.41 * (10^{((SPL/10)-18)})/\Delta f \quad (2)$$

where $$\Delta f = (2^{(1/6)} - 2^{(-1/6)}) fc \text{ for } 1/3 \text{ Octave band} \quad (3)$$

and $$\Delta f = (2^{(1/2)} - 2^{(-1/2)}) fc \text{ for } 1 \text{ Octave band} \quad (4)$$

In block 222, the FE model is simulated under the input load conditions. The FE tool is executed to simulate the model. The FE tool extracts eigenvalues and eigenvectors representing frequencies and mode shapes of the model response to the applied load condition(s). A mass matrix also is extracted. Response frequency analysis may be performed, e.g., using modal acceleration and/or modal superposition analysis methods. Reference is made to U.S. patent application Ser. No. 11/375,225 in which methods are described for frequency response analysis. Additionally or alternatively, FE codes available in NASTRAN, ANSYS and/or LS-DYNA could be used in performing response frequency analysis.

With the critical values of the strain invariants known, the analysis can be checked after every load step to determine if damage has occurred. With respect to quasi-static loading, each load step indicates an increase in the applied load. When the applied loading is an applied frequency, the model is checked for damage initiation as a function of the accumulated cycles. The number of cycles accumulated, the R ratio and applied amplitude (percent of the critical invariant initially applied) are monitored and the accumulated invariant compared to critical strain invariant to assess failure onset. Several commercially available FE code products provide post-processing capabilities to visualize damaged elements. These include ANSYS and ABAQUS (which provide primarily h-element codes) and STRESSCHECK (which provides a p-element code).

Additionally or alternatively, in various implementations of the present disclosure, each gauss point of every element of the model is examined for a given applied frequency with respect to in-situ strain invariants. In-situ values of strain invariants are compared to their critical strain invariant counter-parts. In such manner, it can be determined whether damage exists at a particular location within the structure, and notably, at a particular location within the composite material. Reference is made to U.S. application Ser. No. 11/555,873 filed on Nov. 2, 2006, the disclosure of which is incorporated herein in its entirety, in which systems and methods are described for analyzing load capacity of composite material based on a strain invariant failure theory.

In the present exemplary implementation, when damage has been indicated, the system 200 continues to analyze the structure (as a function of the applied frequency) to assess the evolution of damage vectors as various elements fail. Reference is made to "Damage progression by the element-failure method (EFM) and strain invariant failure theory (SIFT)", by T. E. Tay, S. H. N. Tan, V. B. C. Tan, and J. H. Gosse, Composites and Science Technology 65 (2205) 935-944, the entirety of which is incorporated herein by reference. A damage progression methodology described in the cited reference has been adapted for implementation in accordance with the present disclosure.

In the system 200, the average element values of the total element strain tensor are used to assess element failure. If failure is indicated to have occurred in an element, then nodal forces within the element are replicated and their polarity reversed. A new set of "damage vectors" is then applied directly to the model at the appropriate nodal locations. A slightly different procedure exists for laminated shell elements, but the concept is the same. The matrix phase of composite materials typically cannot be adequately addressed using laminated shell finite elements. As a result, only the fiber phase is addressed. The damage progression algorithm assesses failure within the fiber phase of the laminated shell element and determines what percentage of the plies have failed vs. the total number of plies that can fail. This ratio is a weighting function that operates on the replicated nodal (element) forces prior to their application to the finite element model. As the damage accumulates, the ratio approaches unity since in the limit all of the plies that could fail within the fiber phase have done so.

Once all failures are identified and the damage vectors applied, the model is analyzed further at the applied frequency and the damage assessment process repeated to determine damage redistribution. The steps are repeated until applicable global constraints have been satisfied. This either means that the peak load has been realized (ultimate failure) or some pre-determined criteria for stopping has been realized. The non-arbitrary nature of the damage vector evolution process and the resulting numerical stability make this method particularly appropriate for quasi-static and implicit integration environments.

The foregoing approach simulates the presence of damage in composite materials by replicating the nodal forces of failed elements, reversing their orientations and applying the replicated sets directly to the model itself. Other or additional approaches could be used to simulate damage. For example, damage may be simulated by reducing elastic material properties once element failure is determined to have occurred. In other implementations, embedded meshless finite element models (embedded within conventional finite element models) may be useful for treatment of both damage emergence and fracture, driven using a physics-based failure theory. In such manner, newly separated surfaces could result within a model to simulate transverse cracks, delaminations, etc.

Once a solution is available (final or iterative), the system 200 denotes appropriate measures of interest. This may be accomplished in post-processing in block 244, e.g., through the use of fringe (or contour) plots. Measures of interest, and also the damaged elements (and degree of damage), can be made available for viewing, e.g., via user interface 208.

The foregoing systems and methods make it possible to conduct parametric studies so that optimal selections of materials and geometries can be implemented into the design process. The durability of composite structures may be accurately predicted. Failure modes and their progression under loading can be indicated for laminates and other types of materials. Because the onset of damage initiation is simulated as emerging naturally in the model, it can be assessed without having to impose it onto the model. Thus, emergent damage evolution can be simulated without interference from the analyst. Various implementations can be used to produce more realistic simulations of possible damage states without fitting to existing test data.

Unlike the coupon testing of previously used composite testing methods, coupon testing used in various implementations of the disclosure is not required to meet a similitude requirement that can be difficult in practice to meet. Parametric studies of composite structures can be performed without the tedious process of generating large numbers of test coupons to cover all conditions. The disclosure can be implemented relative to virtually any laminate layup, structural configuration, and/or boundary and/or load conditions. A relatively limited number of mechanical test coupon configurations are needed. Since a physics-based methodology is used for determining whether damage is indicated, various implementations of the disclosure can be applied to conditions not previously studied. This capability can be used to great advantage in the preliminary design of structures. Design cycle time and costs can be reduced while structural performance can be improved.

While various embodiments have been described, those skilled in the art will recognize modifications or variations which might be made without departing from the present disclosure. The examples illustrate the various embodiments and are not intended to limit the present disclosure. Therefore, the description and claims should be interpreted liberally with only such limitation as is necessary in view of the pertinent prior art.

What is claimed is:

1. A method of analyzing durability of a composite structure, comprising:
    performing load-controlled testing of samples of a plurality of materials to be used as part of a structure, the plurality of materials comprising at least one composite material, wherein the load-controlled testing includes determining at least one effective material property of the at least one composite material based on an accumulative invariant approach;
    forming a parametric model of the structure based on the load-controlled testing of the samples and a geometric definition of the structure, wherein the parametric model includes a plurality of elements based on the geometric definition of the structure, and the at least one effective material property of the at least one composite material; and
    determining, using the parametric model, failure characteristics of the structure under load conditions by determining frequency responses of the plurality of elements to data of the load conditions applied to the plurality of elements in the parametric model,
    wherein the at least one effective material property is based on interactions of a plurality of phases of the at least one composite material, the phases including a polymeric matrix phase and a fiber reinforcement phase, and
    wherein determining the failure characteristics of the structure further comprises assessing failure within the fiber reinforcement phase of the at least one composite material and determining a percentage of plies that have failed.

2. The method of claim 1, wherein the determining the at least one effective material property includes determining at least one of:
    a first relationship between critical strain invariants of the materials versus cyclic rates of strain invariant accumulation, and
    a second relationship of load frequencies applied to the materials versus cyclic rates.

3. The method of claim 2, wherein the critical strain invariants of the materials are based on at least one of: temperature, loading rate, and moisture content.

4. The method of claim 2, wherein the first relationship is based on applying a load to samples of the materials until predefined critical invariant values are achieved and wherein the cyclic rates are based on applied frequency of the load and a ratio of minimum stress to maximum stress under the load.

5. The method of claim 1, further including determining whether damage would occur at one or more particular location within the structure.

6. The method of claim 1, wherein the performing the load-controlled testing includes performing simple uni-axial tension tests for each of three lamina configurations for each of the materials.

7. The method of claim 1, wherein the determining the frequency responses involves utilizing load conditions having at least one of: static pressure, thermal loads, pre-loads, vibratory loads, shock loads, and acoustic loads.

8. The method of claim 1, further comprising simulating a progression of damage in the materials of the structure when the data of the load conditions are applied.

9. The method of claim 2, wherein the cyclic rates are based on load frequency applied to the materials and input spectrum.

10. The method of claim 1, further comprising conducting parametric studies, using the model parametric model, to identify combinations of materials and structure geometries associated with failure characteristics within predetermined specifications.

11. The method of claim 1, wherein the determining the frequency responses includes displaying, with a user interface, the failure characteristics of the structure in the format of at least one of: a fringe plot and a contour plot.

12. The method of claim 1, wherein the determining the failure characteristics includes performing a response frequency analysis, wherein the response frequency analysis includes at least one of: modal acceleration and modal superposition.

13. The method of claim 1, wherein load-controlled testing of samples involves a limited number of samples such that studies of composite structures can be performed without generating a large number of test samples since the parametric model is used for determining whether damage is indicated to the plies.

14. A system for analyzing the durability of a structure, the system comprising at least one processor and memory configured to:
    receive at least one effective material property of a plurality of materials from load-controlled testing of samples of the plurality of materials to be used as part of a structure, the plurality of materials comprising at least one composite material, wherein the load-controlled testing includes determining the at least one effective material property of the at least one composite material based on an accumulative invariant approach;
    form a parametric model of the structure based on the load-controlled testing of the samples and a geometric definition of the structure, wherein the parametric model includes a plurality of elements based on the geometric definition of the structure, and the at least one effective material property of the at least one composite material; and
    determine, using the parametric model, failure characteristics of the structure under load conditions by determining frequency responses of the plurality of elements to data of the load conditions applied to the plurality of elements in the parametric model,
    wherein the at least one effective material property is based on interactions of a plurality of phases of the at least one composite material, the phases including a polymeric matrix phase and a fiber reinforcement phase, and
    wherein determining the failure characteristics of the structure further comprises assessing failure within the fiber reinforcement phase of the at least one composite material and determining a percentage of plies that have failed.

15. The system of claim 14, wherein the determining the at least one effective material property includes determining at least one of:
    a first relationship between critical strain invariants of the materials versus cyclic rates of strain invariant accumulation, and
    a second relationship of load frequencies applied to the materials versus cyclic rates.

16. The system of claim 15, wherein the critical strain invariants of the materials are based on at least one of: temperature, loading rate, and moisture content.

17. The method of claim 14, wherein the at least one processor and memory are further configured to simulate a progression of damage in the materials of the structure when the data of the load conditions are applied.

18. The system of claim 14, wherein load-controlled testing of samples involves a limited number of samples such that the system can perform studies of composite structures can be performed without generating a large number of test samples since the parametric model is used for determining whether damage is indicated to the plies.

19. A non-transitory medium containing processor-readable instructions when performed by a processor cause the processor to perform operations of:
receiving at least one effective material property of a plurality of materials from load-controlled testing of samples of the plurality of materials to be used as part of a structure, the plurality of materials comprising at least one composite material, wherein the load-controlled testing includes determining the at least one effective material property of the at least one composite material based on an accumulative invariant approach;
forming a parametric model of the structure based on the load-controlled testing of the samples and a geometric definition of the structure, wherein the parametric model includes a plurality of elements based on the geometric definition of the structure, and the at least one effective material property of the at least one composite material; and
determining, using the parametric model, failure characteristics of the structure under load conditions by determining frequency responses of the plurality of elements to data of the load conditions applied to the plurality of elements in the parametric model,
wherein the at least one effective material property is based on interactions of a plurality of phases of the at least one composite material, the phases including a polymeric matrix phase and a fiber reinforcement phase, and
wherein determining the failure characteristics of the structure further comprises assessing failure within the fiber reinforcement phase of the at least one composite material and determining a percentage of plies that have failed.

20. The non-transitory medium of claim 19, further including processor-readable instructions when performed by a processor cause the processor to simulate a progression of damage in the materials of the structure when the data of the load conditions are applied.

21. The non-transitory medium of claim 19, further including processor-readable instructions when performed by a processor cause the processor to conduct parametric studies, using the model parametric model, to identify combinations of materials and structure geometries associated with failure characteristics within predetermined specifications.

* * * * *

UNITED STATES PATENT AND TRADEMARK OFFICE
CERTIFICATE OF CORRECTION

PATENT NO. : 10,309,883 B2  
APPLICATION NO. : 14/554486  
DATED : June 4, 2019  
INVENTOR(S) : Mostafa Rassaian et al.

Page 1 of 1

It is certified that error appears in the above-identified patent and that said Letters Patent is hereby corrected as shown below:

In the Claims

Column 11, Line 1, in Claim 17, delete "method" and insert -- system --, therefor.

Signed and Sealed this
Twenty-seventh Day of August, 2019

Andrei Iancu
*Director of the United States Patent and Trademark Office*